(12) United States Patent
Yamashita et al.

(10) Patent No.: US 6,277,964 B1
(45) Date of Patent: Aug. 21, 2001

(54) ANTI-PAH MONOCLONAL ANTIBODIES AND CELL LINES PRODUCING THE SAME

(75) Inventors: Nobuhiko Yamashita, Osaka; Kazunobu Miura, Kyoto; Naoya Ichimura, Kyoto; Chiwa Kataoka, Kyoto; Junko Sakaki, Kyoto; Yutaka Ohtani, Kyoto; Hirohisa Kitagawa, Kyoto, all of (JP)

(73) Assignee: Osaka Gas Company Limited, Osaka (JP)

( * ) Notice: Subject to any disclaimer, the term of this patent is extended or adjusted under 35 U.S.C. 154(b) by 0 days.

(21) Appl. No.: 09/265,872

(22) Filed: Mar. 11, 1999

(30) Foreign Application Priority Data

Mar. 12, 1998 (JP) .................................................. 10-061005

(51) Int. Cl.[7] ........................ C07K 16/44; G01N 33/552; G01N 33/535; C12N 5/20
(52) U.S. Cl. ...................... 530/388.9; 435/7.5; 435/7.93; 435/346; 530/808; 530/809; 935/104; 935/110
(58) Field of Search ................................ 530/388.9, 808, 530/809; 935/104, 110; 435/7.5, 7.93, 346

(56) References Cited

U.S. PATENT DOCUMENTS

| | | | |
|---|---|---|---|
| 5,015,586 | 5/1991 | Severn et al. | 436/29 |
| 5,358,851 | 10/1994 | Peck | 435/7.93 |
| 5,449,611 | 9/1995 | Friedman et al. | 435/7.93 |

FOREIGN PATENT DOCUMENTS

| | | |
|---|---|---|
| 2-501351 | 5/1990 | (JP) . |
| WO88/09798 | 12/1988 | (WO) . |
| WO96/13605 | 5/1996 | (WO) . |

OTHER PUBLICATIONS

K. Li et al, Anal. Chem., 71, 302–309, Jan. 1999.*
J. Chagnaud et al, Polycyclic Arom. Compd., 3 (Suppl), 663–672, 1993.*
E. Quelven et al, Polycyclic Aromatic Compounds, 13, 93–103, 1999.*
R. Niessner, Analytical Methods and Instrumentation, 1 (3), 134–144, 1993.*
M. Liu et al, Analytical Letters, 31 (12), 2025–2038, 1998.*
H. Wallin et al, Cancer Letters, 22, 163–170, Jan. 1999.*
Gomes, M., et al., Chem. Res. Toxicol. 3, 307–310 (1990).

* cited by examiner

*Primary Examiner*—Mary E. Ceperley

(57) ABSTRACT

The present invention provides monoclonal antibodies suitable for monitoring polycyclic aromatic hydrocarbons (PAHs) by an immunoassay, hybridoma cell lines producing said antibodies, and an immunoassay for analyzing PAHs in a sample using said monoclonal antibodies. In addition, the present invention provides PAH conjugates useful as an immunogen in preparing said antibodies and as a standard substance in a competitive assay.

3 Claims, 11 Drawing Sheets

US 6,277,964 B1

ANTI-PAH MONOCLONAL ANTIBODIES AND CELL LINES PRODUCING THE SAME

FIELD OF THE INVENTION

The present invention relates to monoclonal antibodies having a high affinity for polycyclic aromatic hydrocarbons (PAHs) such as phenanthrene and benzo [a]pyrene, hybridoma cell lines producing said monoclonal antibodies, and immunoassays for monitoring and quantifying the amount of PAHs present in the environment with a high sensitivity using said monoclonal antibodies.

The present invention also relates to PAH conjugates useful as an imunogen in preparing said antibodies and as a standard substance in a competitive assay.

DESCRIPTION OF THE PRIOR ART

In the measurement of PAHs existing in the environment, sixteen bicyclic to hexacyclic standard compounds such as naphthalene, phenanthrene and benzo [a]pyrene are generally analyzed, which are defined by the U.S. Environmental Protection Agency (EPA), although PAHs include a great number of compounds.

Methods for measuring PAHs in a sample include Soxlet extraction with toluene, gas chromatography, high performance liquid chromatography, thin layer chromatography, immunoassay, and the like.

However, Soxlet extraction with toluene measures the total amount of oil components including asphaltenes, resins, etc. in addition to all PAls contained in a sample, and therefore, it is impossible to analyze each individual PAR component.

Gas chromatography and high performance liquid chromatography can analyze and quantify all the sixteen PAH components defined by the EPA, contained in a sample. However, these methods can not monitor a number of samples concurrently, and therefore, they are mainly used for a precise analysis in a laboratory.

On the other hand, thin layer chromatography and immunoassaycan rapidly analyze a number of samples concurrently. However, these methods are inferior to gas chromatography and high performance liquid chromatography in terms of their resolving powers, and therefore, it is difficult to distinguish all the sixteen PAH components defined by the EPA. Accordingly, these methods are used, when the purpose of the measurement is merely the distinguishment of the groups of bi-, tri-, tetra-, penta- and hexa-cyclic components of PAHs or the grasp of the relative concentrations of the groups of the above components.

As described above, an analytic method used varies depending on the purpose of the measurement, and an immunoassay is suitable for a field monitoring where the rapid measurement of many samples is required.

In monitoring PAHs in an exhaust gas or a drained water or PAHs in.a contaminated soil by an immunoassay, the following technical problems may arise:

(1) In general, it is difficult to prepare an antibody against a low molecular antigen such as PAHs;
(2) The structures of the sixteen standard PAHs greatly resemble to each other, and. therefore, it is difficult to obtain an antibody which distinguishes each individual structure of them; and
(3) PAHs are slightly soluble in water and it is necessary to carry out an antigen-antibody reaction in an organic solvent, but the antibody is mainly comprised of a high molecular weight protein, and therefore, it is likely to lose its activity in the organic solvent.

U.S. Pat. No. 5,358,851 discloses a polyclonal antibody prepared by conjugating p-tolylacetic acid with bovine γ-globulin and using the resulting conjugate as an immunogen. The patent specification also discloses a method for analyzing the presence or the amount of aromatic ring-containing compounds, such as benzene, toluene and xylene, in a sample using the polyclonal antibody.

U.S. Pat. No. 5,449,611 discloses a monoclonal antibody prepared by conjugating β-methylnaphthalene with bovine serum albumin and using the resulting conjugate as an immunogen. The patent specification also discloses a method for analyzing the presence of PAHs in a sample using the monoclonal antibody.

In addition, M. Gomes and R. M. Santella [Chem. Res. Toxicol. 3, pp.307–310 (1990)] discloses a monoclonal antibody prepared by using 6-aminobenzo [a]pyrene bound to bovine serum albumin as an immunogen. The document describes that the monoclonal antibody not only reacts with benzo [a]pyrene, but also cross-reacts with metabolic products thereof and some of other PAHs.

However, the polyclonal and monoclonal antibodies disclosed in these[]documentsare not satisfactory in terms of their specificity and affinity for the antigen, when used for monitoring PAHs.

SUMMARY OF THE INVENTION

One object of the present invention is to solve the technical problems as described above and to provide a monoclonal antibody more suitable for monitoring PARs by an immunoassay.

Another object of the present invention is to provide a hybridoma cell line producing said antibody, and an immunoassay for analyzing PAHs in a sample using said monoclonal antibody.

A further object of the present invention is to provide a PAH conjugate useful as an immunogen in preparing said antibody and as a standard substance in a competitive assay.

According to the present invention, these and other objects are accomplished by a monoclonal antibody specifically recognizing polycyclic aromatic compounds selected from the group consisting of monoclonal antibodies PAH-1, PAH-3, PAH-6 and PAH-7.

Also, the present invention provides a hybridoma cell line producing the above monoclonal antibody, which is selected from the group consisting of hybridomas PAH-1, PAH-3, PAH-6 and PAH-7.

Furthermore, the present invention provides an immunoassay for analyzing polycyclic aromatic compounds in a sample, which comprises:

(a) carrying out an antigen-antibody reaction of a sample containing polycyclic aromatic compounds with the above monoclonal antibody in an aqueous solution containing an organic solvent; and
(b) detecting the polycyclic aromatic compounds bound to the antibody.

In addition, the present invention provides a conjugate of the following formula (1):

$$\text{Ar}-\text{CO}-(\text{CH}_2)_n-\text{CONH}-\text{Z} \qquad (1)$$

wherein Ar is a tricyclic, tetracyclic or pentacyclic aromatic compound, n is an integer of 1 to 3, and Z is a carrier protein or a labeling substance.

The present inventors established hybridoma cell lines producing anti-PAH monoclonal antibodies suitable for the measurement of PAHs, by binding PAHs to carrier proteins through a spacer to prepare novel PAH conjugates, immunizing an animal using the conjugates asan immunogen, fusing antibody-producing cells of the immunized animal with myeloma cells to prepare hybridoma cell lines, and selecting the hybridoma cell lines suitably. Also, we could construct an immunoassay for the measurement of PAHs using the monoclonal antibodies.

DETAILED DESCRIPTION OF THE INVENTION

Figure 1:
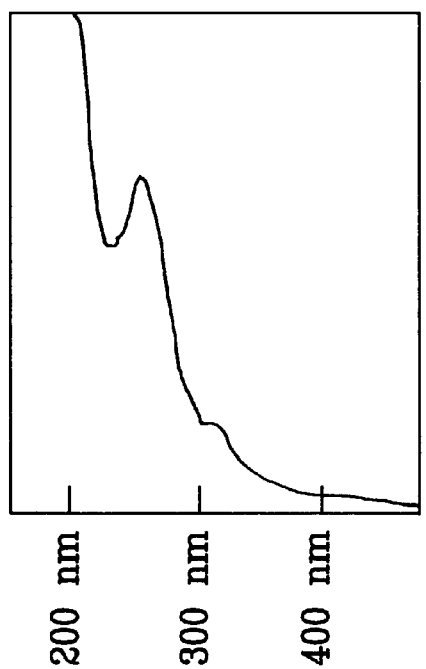
FIG. 1 is a chart showing an absorption spectrum of the phenanthrene-myoglobin conjugate.

If an animal is immunized with a low molecular antigen, in general, a method for enhancing an antigen recognition by a living body is employed which comprises binding the antigen to other proteinaceous antigen (carrier protein) through a suitable cross-linking reagent and using the resulting conjugate as an immunogen.

The present inventors found that the objective anti-PAH monoclonal antibodies can be obtained by employing as an immunogen a conjugate of the following formula (2):

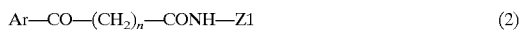

$$Ar—CO—(CH_2)_n—CONH—Z1 \quad (2)$$

wherein Ar is a tricyclic, tetracyclic or pentacyclic aromatic compound, n is an integer of 1 to 3, and Z1 is a carrier protein.

In the conjugate of the above formula (2), the tricyclic, tetracyclic or pentacyclic aromatic compound includes the tricyclic to pentacyclic standard compounds defined by EPA such as acenaphthylene, acenaphthene, fluorene, phenanthrene, anthracene, fluoranthene, pyrene, benzo[a] anthracene, chrysene, benzo[b]fluoranthene, benzo[k] fluoranthene, benzo[a]pyrene and dibenzo[a,h]anthracene.

The carrier protein includes myoglobin, bovine serum albumin (BSA), keyhole limpet hemocyanin (KLH), and the like.

The PAH conjugate of the above formula (2) can be prepared, for example, in the following manner. Firstly, PAH and a compound of the following formula (3):

$$XCO—(CH_2)_n—COOAlk \quad (3)$$

wherein X is a halogen atom, Alk is a lower alkyl group, and n is as defined above, are allowed to react by the Friedel-Crafts reaction to obtain a compound of the formula: PAH—CO—(CH$_2$)$_n$—COOAlk. Then, the terminal ester group of this compound is hydrolyzed to form a carboxyl group, and the terminal carboxyl group is allowed to react with N-hydroxysuccinimide to obtain a N-hydroxysuccinimido ester (PAH derivative). Finally, the PAH derivative is allowed to react with a carrier protein to obtain the conjugate of the above formula (2).

The above Friedel-Crafts reaction, hydrolysis, esterification, and the reaction of the PAH derivative with the carrier protein may be carried out according to reaction conditions well known in the art.

The PAH conjugate prepared as described above is used as an immunogen to immunize an animal. Animals to be immunized may be, for example, mice, rats, rabbits or goats. Immunization may be carried out by administering 4 to 40 mg of the PAH conjugate into the peritoneal cavity of an animal, 3 or 4 times at intervals of 2 to 3 weeks.

After three days from the final immunization, the antibody-producing cells are recovered from the immunized animal. The antibody-producing cells may be, for example, spleen cells or lymph node-derived B cells. The antibody-producing cells are fused with myeloma cells by a conventional method. The myeloma cells may be those derived from mice, rats or humans. The cell fusion may be carried out using, for example, a polyethylene glycol method or an electrical fusion method.

The selection of hybridomas obtained by the cell fusion may be carried out, for example, by radioimmunoassay, enzyme-labeled immunoassay (ELISA) or fluorescence-labeled immunoassay. Thus, the PAH conjugate is allowed to react with a supernatant of hybridoma cultures, wells containing hybridomas which produce an anti-PAH antibody are selected, and the hybridomas in the wells are cloned by a limiting dilution method to establish hybridoma cell lines.

The preparation of the monoclonal antibody can be carried out, for example, in the following manner. The established hybridoma cell lines are implanted into the peritoneal cavity of a mouse previously administered with pristan (2,6,10,14-tetramethylpentadecan), and the ascites fluid of the mouse containing the monoclonal antibody is recovered after 10 to 14 days from the implantation. The monoclonal antibody can be easily recovered from the ascites fluid by ammonium sulfate precipitation, ion-exchange chromatography, affinity chromatography, or the like.

It is possible to determine PAis in a sample using the resulting monoclonal antibody. Such a measurement includes radioimmunoassay (RIA), enzyme immunoassay (EIA), fluoroimmunoassay (FIA), and the like.

Competitive and solid phase methods are known in RIA. In the competitive method, a sample to be determined is firstly allowed to react with a known antibody and then with a known antigen labeled with an isotope. Next, an anti-γ-globulin antibody is added to and allowed to react with the mixture, and the radioactivity of the precipitated material is measured. If a sample contains a large amount of an antigen to be detected, a known antibody will react with the antigen in the sample and therefore will not react with the known antigen labeled with an isotope added later. Accordingly, the radioactivity of the precipitated material is low. To the contrary, if a sample contains a small amount of an antigen, a known antibody will react with a large amount of the known antigen labeled with an isotope, and therefore, the radioactivity. of the precipitated material is high. By measuring the radioactivity as described above, it is possible to quantify an antigen in a sample.

In the solid phase method, a known antibody is bound to polystyrene or glass beads. The antibody bound to beads is allowed to react with a sample to be determined and then with a second antibody labeled with an isotope. If anantigen to be detected is present in the sample, the second labeled antibody will bind to the beads, and therefore, it is possible to quantify the antigen in the sample by measuring the radioactivity on the beads. In this case, the amount of the antigen is proportional to that of the radioactivity.

EIA is carried out in a similar manner to a RIA solid phase method, but uses an enzyme for the labeling of an antibody instead of an isotope. FIA uses a fluorescent pigment for the labeling instead of an isotope or an enzyme.

An isotope such as $^{125}I$, $^{57}Co$, $^{75}Se$ or $^{32}P$ is used for RIA, an enzyme such as alkaline phosphatase, glucoacylase, galactosidase, peroxidase or acetylcholinesterase is used for EIA, and a derivative of fluorescein, rhodamine, dansyl or the like is used for FIA, as a labeling substance for the above materials.

Although the above antigen-antibody reaction can be carried out in an aqueous solution, it is convenient to carry out the reaction in an aqueous solution containing an organic solvent. The organic solvent is preferably water-soluble and includes, for example, methanol, ethanol, isopropanol, n-propanol, butanol, acetone, acetonitrile and dimethyl sulfoxide. The antigen-antibody reaction is preferably carried out in an aqueous solution containing less than 70 vol. % of methanol, less than 70 vol. % of ethanol, less than 50 vol. % of acetonitrile or less than 50 vol. % of dimethyl sulfoxide, based on the whole solvent.

Also, in the competitive assay, it is advantageous to use, as a standard substance, a conjugate of the following formula (4):

$$Ar-CO-(CH_2)_n-CONH-Z2 \quad (4)$$

wherein Ar is a tricyclic, tetracyclic or pentacyclic aromatic compound, n is an integer of 1 to 3, and Z2 is a labeling substance.

In the above formula (4), Ar is the same as that described for the above formula (2).

On the other hand, the labeling substance of Z2 includes biotin, peroxidase, alkaline phosphatase, and the like.

The PAK conjugate of the above formula (4) can be prepared in a similar manner to that for preparing the PAH conjugate of the above formula (2). Thus, aN-hydroxysuccinimido ester (PAH derivative) prepared by binding N-hydroxysuccinimide to PAH through a spacer is allowed to react with a labeling substance, according to reaction conditions well known in the art, to obtain the conjugate of the above formula (4).

Example

The present invention is illustrated more specifically based on the following examples, but it is not limited thereto.

Example 1
Preparation of PAH Conjugate
(1) Introduction of spacer molecule into phenanthrene (Phe)

A phenanthrene derivative with a spacer molecule introduced into phenanthrene was synthesized according to the following reaction formula I, as the first stage for preparing a conjugated antigen to be administered to an immunization animal.

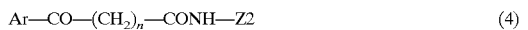

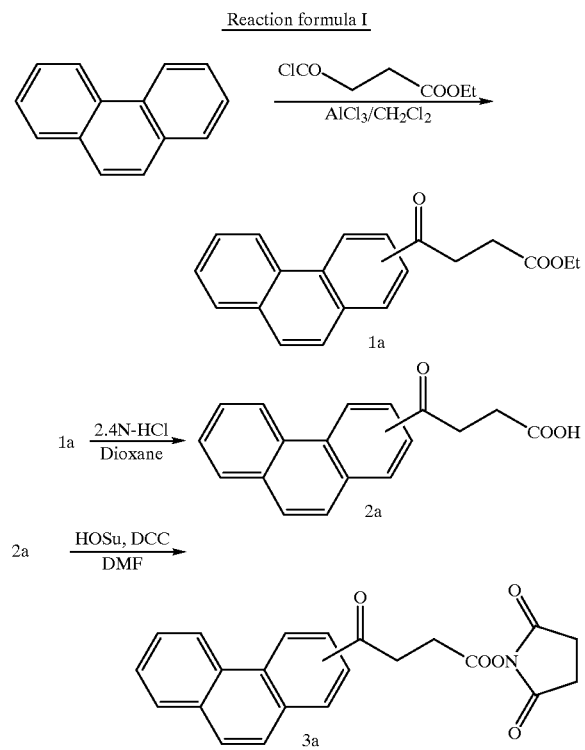

Firstly, phenanthrene-4-oxobutyric acid ethyl ester (compound 1a) was synthesized from phenanthrene. Aluminium chloride (3.6 g; 27 mmol) was added to an ice-cooled solution of monoethyl succinyl chloride (3.5 ml; 25 mmol) in dichloromethane (60 ml), and the mixture was stirred for 30 minutes. Phenanthrene (4.0 g; 22 mmol) was added to the ice-cooled solution, and the mixture was warmed to room temperature and stirred for 2 days. The reaction mixture was poured onto ice and extracted with dichloromethane. The organic layer was washed with water and the solvent was then removed under a reduced pressure. The residue was purified by silica gel chromatography (eluted with 1:10 of dichloromethane:hexane) to obtain 2.46 g (36% yield) of compound 1a as a position-isomer mixture.

Next, phenanthrene-4-oxobutyric acid (compound 2a) was synthesized from compound 1a. Compound 1a (2.4 g; 7.8 mmol) was dissolved in a mixture of dioxane (15 ml) and 2.4 N aqueous hydrochloric acid (15 ml), and the mixture was stirred for 8 hours under reflux with heating. The reaction mixture was extracted with dichloromethane, the organic layer was washed with water, and the solvent was then removed under a reduced pressure. The residue was washed with diethyl ether to obtain 1.43 g (66% yield) of compound 2a as a position-isomer mixture.

Finally, phenanthrene-4-oxobutyric acid N-hydroxysuccinimide ester (compound 3a) was synthesized from compound 2a. Compound 2a (560 mg; 2 mmol) and N-hydroxysuccinimide (240 mg; 2 mmol) was dissolved in dimethylformamide (2 ml). The solution was ice-cooled and dicyclohexylcarbodiimide (460 mg; 2.2 mmol) was added to the solution. The solution was then warmed to room temperature and stirred for 16 hours. The precipitate formed was removed by filtration and the filtrate was concentrated under a reduced pressure. The residue was then purified by silica gel chromatography (eluted with 4:1 of dichloromethane:hexane). The fractions containing the desired product were concentrated and the concentrate was crystallized with diethyl ether to obtain 378 mg (50% yield) of compound 3a as a position-isomer mixture.

Positions into which the spacer was introduced were presumed by reference to the description of George A. Olah, "Friedel-Crafts and Related Reaction", Vol.III, Part I (1964). As a result, it was presumed that the spacer was introduced in a high possibility into the 9-position of phenanthrene as shown below:

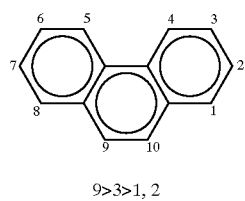

9>3>1, 2

(2) Introduction of spacer molecule into benzo[a]pyrene (Bp)

A benzo[a]pyrene derivative with a spacer molecule introduced into, benzo[a]pyrene was synthesized according to the following reaction formula II, in the same manner as described in the above section (1).

Reaction formula II

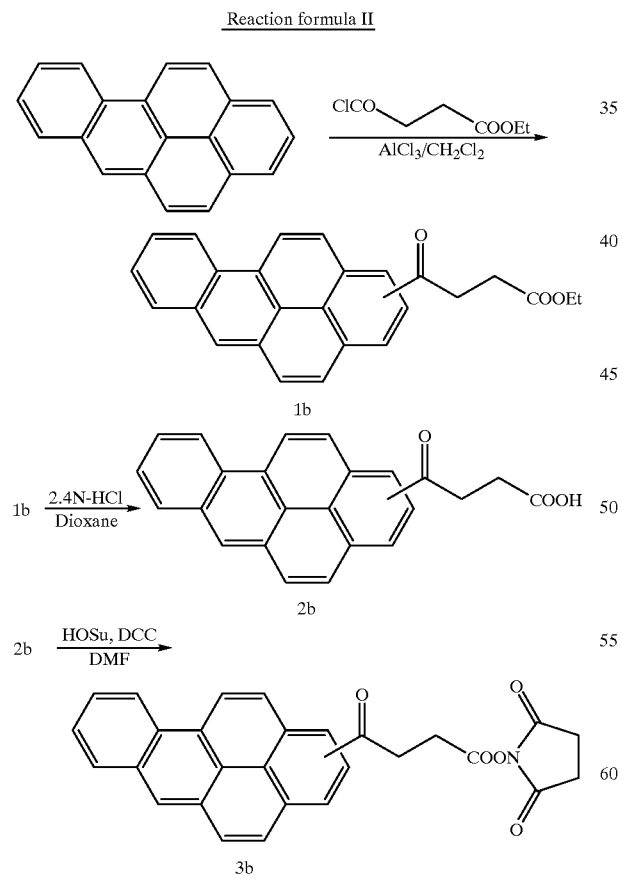

Firstly, benzo[a]pyrene-4-oxobutyric acid ethyl ester (compound 1b) was synthesized from benzo[a]pyrene. Aluminium chloride (920 mg; 7 mmol) was added to an ice-cooled solution of monoethyl succinyl chloride (1.24 ml; 6.3 mmol) in dichloromethane (15 ml), and the mixture was stirred for 30 minutes. Benzo[a]pyrene (1.45 g; 5.8 mmol) was added to the ice-cooled solution, and the mixture was warmed to room temperature and stirred overnight. The reaction mixture was poured onto ice and extracted with dichloromethane. The organic layer was washed with water and the solvent was then removed under a reduced pressure. The residue was purified by silica gel chromatography (eluted with 1:2 of dichloromethane:hexane) to obtain 932 mg (43% yield) of compound 1b as a position-isomer mixture.

Next, benzo[a]pyrene-4-oxobutyric acid (compound 2b) was synthesized from compound 1b. Compound 1b (890 mg; 2.3 mmol) was dissolved in a mixture of dioxane (5 ml) and 2.4 N aqueous hydrochloric acid (5 ml), and the mixture was stirred for 6 hours under reflux with heating. The reaction mixture was extracted with dichloromethane, the organic layer was washed with water, and the solvent was then removed under a reduced pressure. The residue was washed with dichloromethane to obtain 555 mg (67% yield) of compound 2b as a position-isomer mixture.

Finally, benzo[a]pyrene-4-oxobutyric acid N-hydroxysuccinimide ester (compound 3b) was synthesized from compound 2b. Compound 2b (353 mg; 1 mmol) and N-hydroxy-succinimide (115 mg; 1 mmol) was dissolved in dimethylformamide (3 ml). The solution was ice-cooled and dicyclohexylcarbodiimide (248 mg; 1.20 mmol) was added to the solution. The solution was then warmed to room temperature and stirred for 16 hours. The precipitate formed was removed by filtration and the filtrate was concentrated under a reduced pressure. The residue was then purified by silica gel chromatography (eluted with 4:1 of dichloromethane:hexane). The fractions containing the desired product were concentrated and the concentrate was washed with 2-propanol to obtain 359 mg (80% yield) of compound 3b as a position-isomer mixture.

Positions into which the spacer was introduced were presumed by reference to the description of Olah (above-mentioned). As a result, it was presumed that the spacer was introduced in a high possibility into the 3-position of benzo [a]pyrene as shown below:

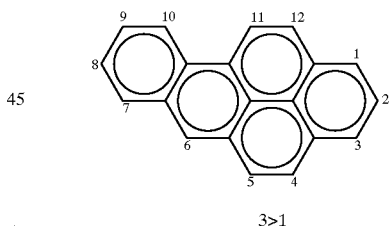

3>1

(3) Preparation of PAH conjugate with carrier protein

The phenanthrene derivative and benzo[a]pyrene derivative prepared in the above sections (1) and (2), respectively, were bound to myoglobin, bovine serum albumin (BSA) or keyhole limpet hemocyanin (KLH) as a carrier protein, through the spacer of the derivatives.

A solution of phenanthrene-4-oxobutyric acid N-hydroxysuccinimide ester (compound3a) (3 mg) dissolved in DMSO (30 μl) was mixed with a solution of myoglobin, BSA or KLH (1.6 mg) dissolved in 25 mM phosphate buffer, pH 8.0 (400 μl), and the mixture was allowed to stand at room temperature for 2 hours. The mixture was then treated by gel filtration chromatography (using NAP-5 of Pharmacia) to remove unreacted materials and the protein concentration was quantified by a protein assay.

A similar preparation to that described above was carried out using benzo[a]pyrene-4-oxobutyric acid N-hydroxysuccinimide ester (compound 3b).

Next, the resulting conjugate solution was adjusted to a concentration of 20 μg/ml with 25 mM phosphate buffer, pH 8.0, and its absorption spectrum was analyzed. The absorbance was measured at a particular wavelength (310 nm for phenanthrene conjugate and 300 nm for benzo[a]pyrene conjugate) and the molecular number of the compound introduced into the conjugate was presumed.

Figure 2:
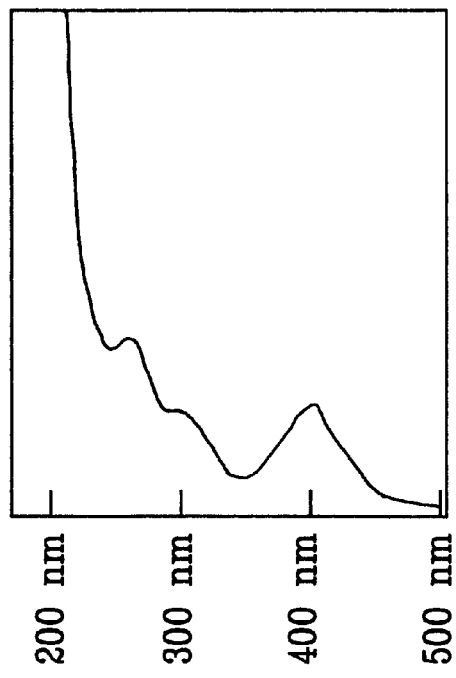
FIG. 2 is a chart showing an absorption spectrum of the benzo[a]pyrene-myoglobin conjugate.
Figure 3:
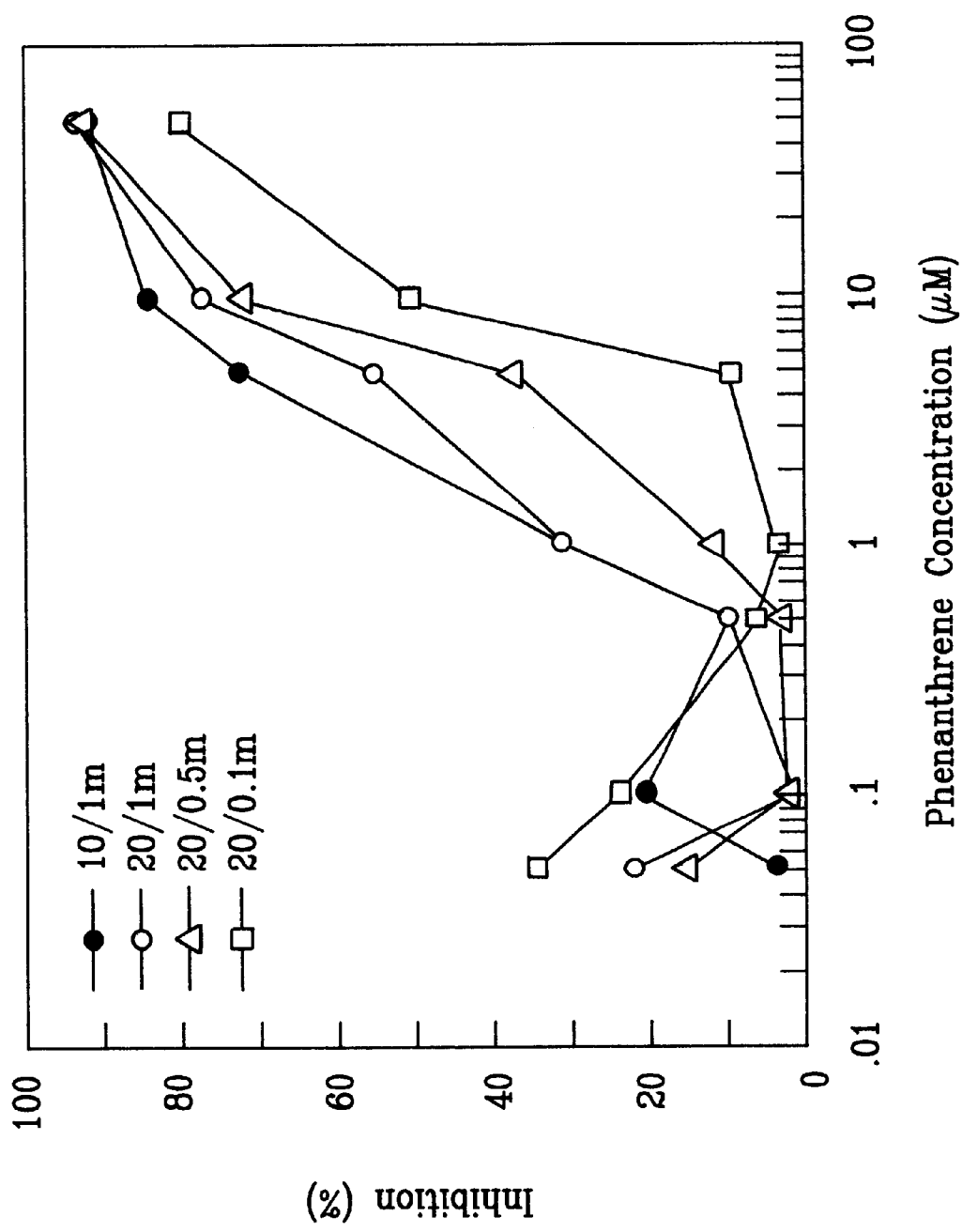
FIG. 3 is a graph showing a PAH amount (unlabeled PAH added)-reaction curve when using monoclonal antibody MPAH-1.
Figure 4:
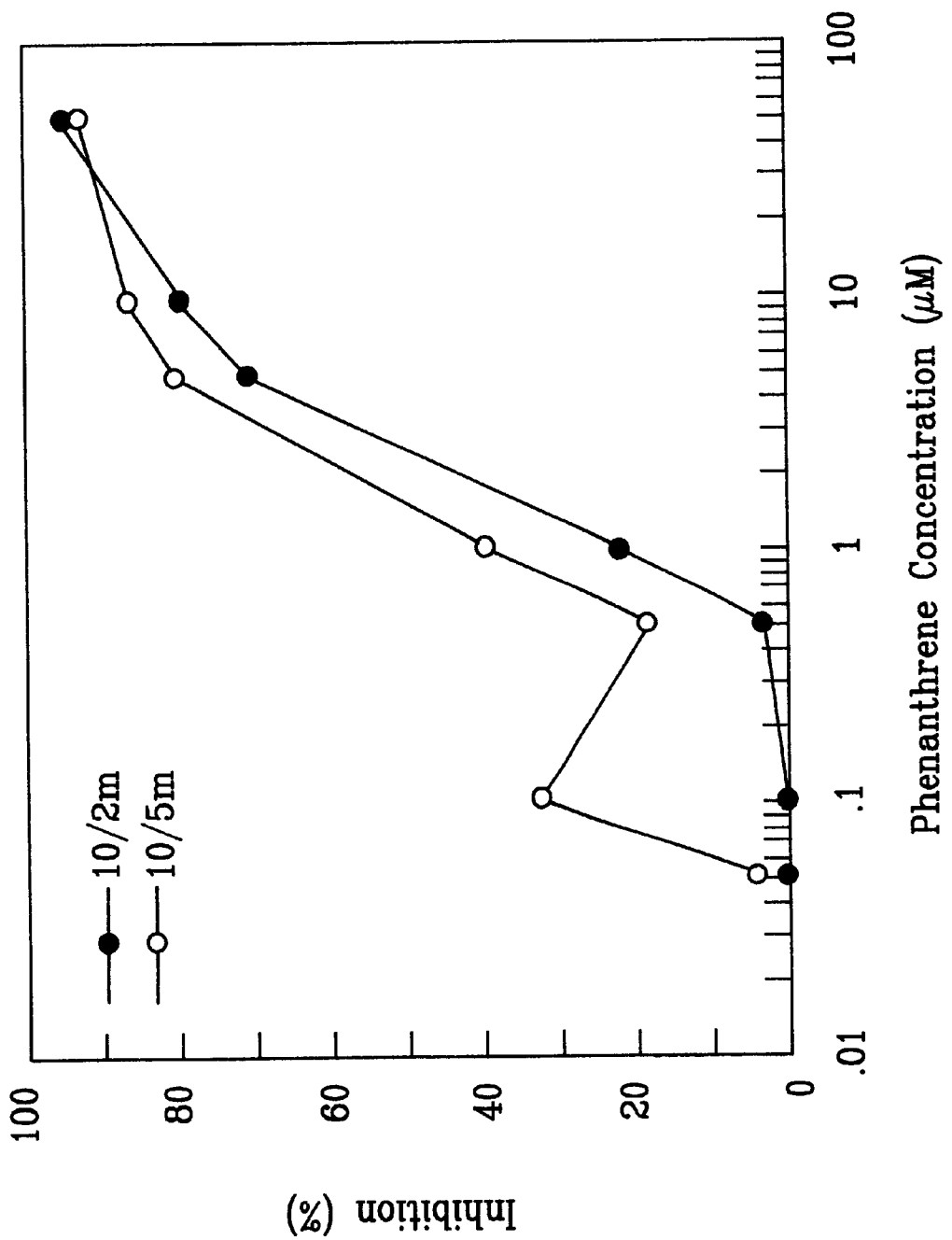
FIG. 4 is a graph showing a PAR amount (unlabeled PAH added)-reaction curve when using monoclonal antibody MPAH-3.
Figure 5:
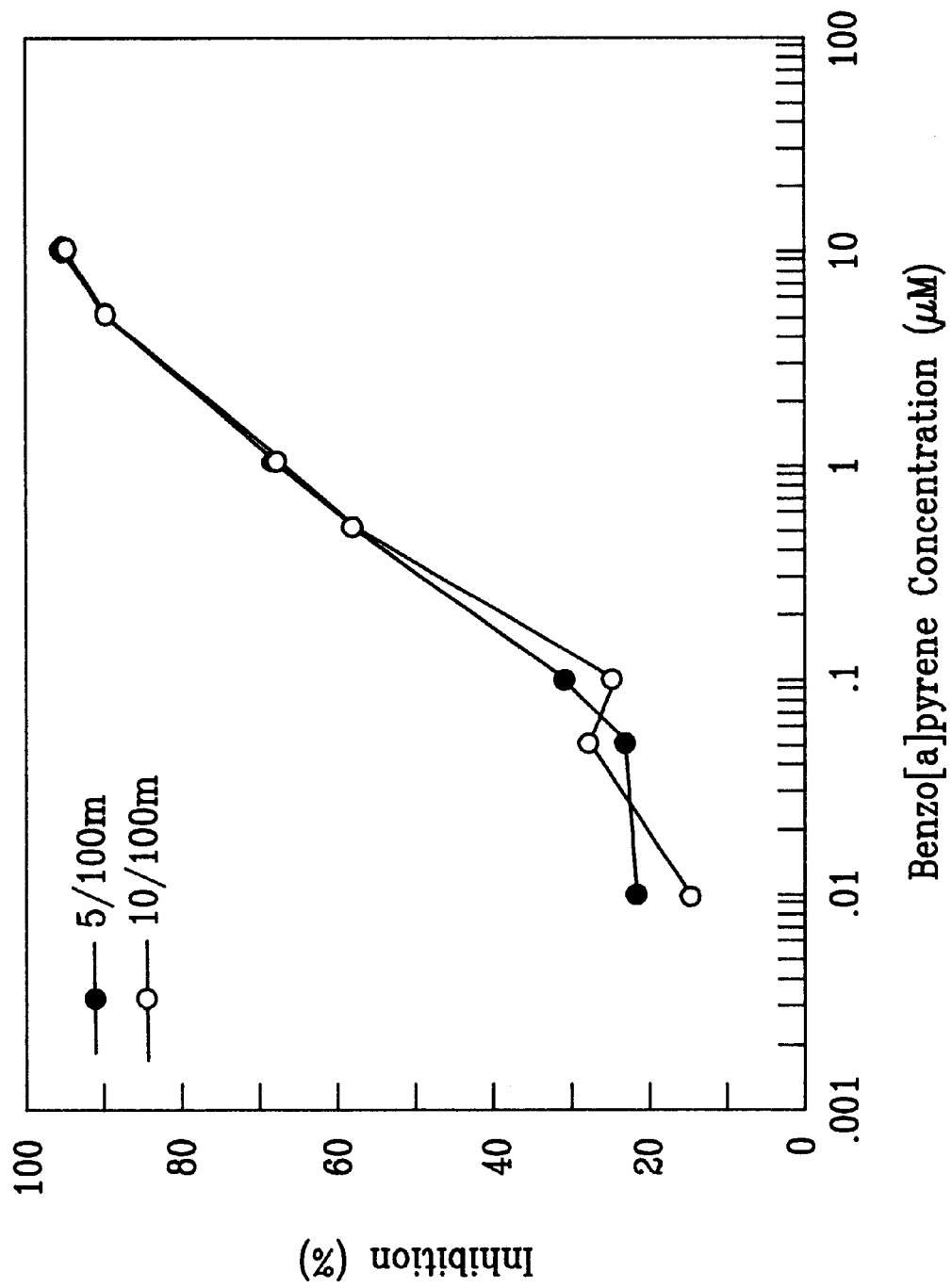
FIG. 5 is a graph showing a PAH amount (unlabeled PAH added)-reaction curve when using monoclonal antibody MPAH-6.
Figure 6:
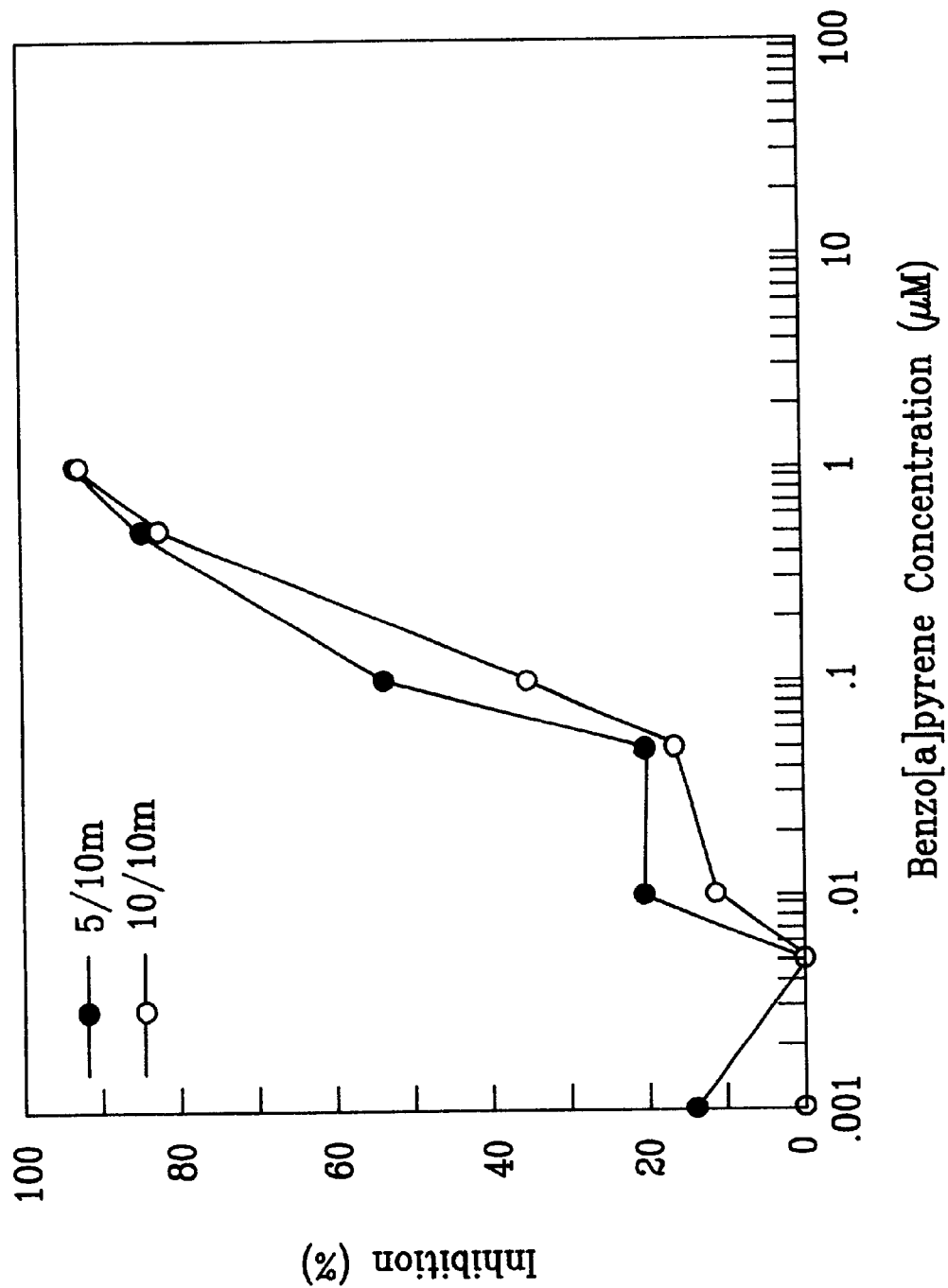
FIG. 6 is a graph showing a PAH amount (unlabeled PAH added)-reaction curve when using monoclonal antibody MPAH-7.

The absorption spectra of the phenanthrene-myoglobin conjugate and benzo[a]pyrene-myoglobin conjugate are shown in FIGS. 1 and 2, respectively. Also, the presumed molecular number of the compound-introduced per myoglobin molecule in each conjugate is shown in Table 1 below:

TABLE 1

Molecular number of compound introduced per myoglobin molecule

| Compound introduced | Molecular number |
|---|---|
| Phenanthrene | 60 |
| Benzo[a]Pyrene | 24 |

(4) Preparation of PAH conjugate with labeling substance

The phenanthrene derivative and benzo[a]pyrene derivative prepared in the above sections (1) and (2), respectively, were bound to peroxidase or alkaline phosphatase as a labeling substance, through the spacer of the derivatives.

A solution of phenanthrene-4-oxobutyric acid N-hydroxysuccinimide ester (compound 3a) (3 mg) dissolved in DMSO (30 μl) was mixed with a solution of peroxidase or alkaline phosphatase (1.6 mg) dissolved in 25 mM phosphate buffer, pH 8.0 (400 μl), and the mixture was allowed to stand at room temperature for 2 hours. The mixture was then treated by gel filtration chromatography (using NAP-5 of Pharmacia) to remove unreacted materials and the protein concentration was quantified by a protein assay.

A benzo[a]pyrene conjugate with a labeling substance was prepared in a similar manner to that described above, using benzo[a]pyrene-4-oxobutyric acid N-hydroxysuccinimide ester (compound 3b).

Example 2
Preparation of anti-PAH monoclonal antibodies
(1) Immunization of mouse Mice were immunized with four conjugates obtained by combining BSA and KLH with phenanthrene and benzo[a]pyrene. The phenanthrene conjugate and benzofalpyrene conjugate containing BSA or KLH as a carrier protein were thoroughly emulsified in an adjuvant (Ribi Adjuvant system R-730), and the resulting emulsions were then administered into the peritoneal cavity (150 μl) and into the hind-foot pad (50 μl) of BALB/c mice (7 to 8 weeks age, male) to immuno-sensitize the mice. After about one week from the immunization, blood was taken from the tail vein, and the antibody titer was measured by ELISA. Booster immunizations were carried out at intervals of about 2 to 3 weeks, and the change of the antibody titer was observed by measuring the antibody titer in blood after the passage of one week from each booster immunization.
(2) Cell fusion Mice in which a high level production of an antibody against phenanthrene or benzo[a]pyrene was confirmed were finally immunized. After 3 days from the final immunization, the spleen was removed from the mice and spleen cells were prepared. Myeloma cells (X63/Ag.8.653) and the spleen cells were mixed in a ratio of 1:5, and the cell fusion was carried out by a polyethylene glycol (PEG) method. The cells were suspended into a RPMI-1640 medium containing 10% FCS to which HAT (hypoxanthine, aminopterin and thymidine) were added, seeded in a 96-well culturing plate in a density of 2 to $5 \times 10^5$ cells/well, and cultivated under 5% $CO_2$ at 37° C.
(3) Screening and cloning of antibody-producing hybridomas After 10 to 20 days from the cell fusion, the antibody titer was determined using the supernatant of the culture in the well in which proliferation of a clone was observed. The determination of the antibody titer was carried out by an enzyme immunoassay.

Phenanthrene-introduced myoglobin was used for an antibody against phenanthrene and benzo[a]pyrene-introduced myoglobin was used for an antibody against benzo[a]pyrene, as an antigen for the screening. Phenanthrene-introduced myoglobin or benzo[a]pyrene-introduced myoglobin was diluted with PBS so that the concentration of the introduced phenanthrene or benzo[a]pyrene was 5, 1, 0.5 and 0.1 μg/ml. The 5 μg/ml solution was added to 4 wells of line A in a 96-well microtiter plate (Costar) in the amount of each 50 μl aliquot. Next, the 1 μg/ml solution was added to 4 wells of line B in the plate in the amount of each 50 μl aliquot. Similarly, the 0.5 and 0.1 μg/ml solutions were added to the wells of lines C and D, and PBS (−) was added to the wells of line E in the amount of each 50 μl aliquot. The antigen and antibody in the wells were allowed to react at 37° C. for one hour. After these wells were washed with PBS, 1% gelatin-PBS (−) solution (300 μl) was added to the wells, and the wells were blocked at 37° C. for 2 hours.

After each well was washed with PBS, the supernatant of the culture diluted with 1 mg/ml BSA or KLH to 10-, 100-, 1000- or 10000-fold (50 μl) was added to the well and allowed to react at 37° C. for one hour. Then, peroxidase-labeled anti-mouse IgG antibody (recognizing γ-chain)(KPI Inc.) diluted with 0.1% gelatin-PBS (−) solution to 3000-fold (100 μl) was added to the well and allowed to react at room temperature for one hour. After each well was thoroughly washed, a 0.1% o-phenylenediamine solution containing 0.5% $H_2O_2$ (50 μl) was added to the well and the well was allowed to stand at room temperature for 15 minutes. Then, the reaction was terminated by adding 2M sulfuric acid and the absorbance was measured (measuring wavelength 490 nm and control wavelength 595 nm).

Hybridomas in the wells, in which the production of an antibody was confirmed, were cloned by a limiting dilution method. The hybridomas were cultivated in a RPMI-1640 medium containing 15% fetal bovine serum.

By the above procedures, totally 4 clones of hybridomas were established, i.e. 2 clones of hybridomas (PAH-1 and PAH-3) producing an anti-phenanthrene monoclonal antibody and 2 clones of hybridomas (PAH-6 and PAH-7) producing an anti-benzo[a]pyrene monoclonal antibody.

These four hybridomas PAH-1, PAH-3, PAH-6 and PAH-7 (producing monoclonal antibodies MPAH-1, MPAH-3, MPAH-6 and MPAH-7, respectively) were deposited to National Institute of Bioscience and Human-Technology, Agency of Industrial Science and Technology (1–3, Higashi 1-chome Tsukuba-shi Ibaraki-ken 305, JAPAN) under the terms of the Budapest Treaty on Feb. 6, 1998, and obtained the accession numbers of FERM BP-6246, FERM BP-6247, FERM BP-6248 and FERM BP-6249, respectively.

(4) Analysis of isotype

An isotype analysis of the antibodies produced by the established hybridomas was carried out using the phenanthrene(Phe)-BSA or benzotalpyrene(Bp)-BSA conjugate (immunogen) as a solid phase antigen and using Mouse Typer Kit (Bio-Rad Laboratories). The results are as shown in Table 2 below:

TABLE 2

Isotype of antibodies produced by established hybridomas

| Hybridoma Name | Type of produced anitbody |
|---|---|
| Hybridoma producing anti-Phe antibody | |
| PAH-1 (Clone 6-5C-14E) | IgG2a (κ) |
| PAH-1 (Clone 8-4D-65D) | IgG2a (κ) |
| Hybridoma producing anti-Bp antibody | |
| PAH-6 (Clone 19-2C-54B) | IgG2a (λ) |
| PAH-7 (Clone 22-2C-611B) | IgG2a (κ) |

(5) Large-scale preparation and purification of monoclonal antibody

Pristan (2,6,10,14-tetramethylpentadecan; Wako Junyaku Co.) (0.5 ml) was intraperitoneally injected to mice, and the mice were bred over 2 weeks. Monoclonal antibody-producing hybridomas which were previously proliferated were recovered and diluted with DMEM to a cell density of about $4 \times 10^6$ cells/ml. The cell solutions (0.5 ml each) were intraperitoneally injected into the mice. After 1 to 3 weeks from the injection, the abdomen of the mice was cut out and ascites fluid was recovered with a Pasteur pipet. The ascites fluid taken was mixed with an equal volume of a hemolysate, and the mixture was then centrifuged at 2,000 rpm for 10 minutes. The resulting supernatant was used as a monoclonal antibody solution.

From the monoclonal antibody solutions thus obtained, monoclonal antibodies were purified by Protein A column chromatography using a mouse IgG purification kit [Affigel Protein A MAPS-II; Bio-Rad Laboratories Co. Ltd.].

Example 3
Determination of PAH by ELISA
(1) Investigation of conditions for measuring systems using monoclonal antibodies Various concentrations of purified antibodies (1, 5 and 10 μg/ml: prepared using PBS (−)) (50 μl) were added to wells of a 96-well ELISA plate and allowed to stand at 37° C. for one hour. Then, 1% gelatin-PBS (−) solution (300 μl each) was added to the wells, and the wells were blocked at 37° C. for 2 hours and used as a solid phase antibody.

Next, biotin-labeled Phe or biotin-labeled Bp adjusted to the concentration ranges of 0.008 μM to 0.8 μM (prepared using 50% MeOH) (25 μl) and unlabeled PAH adjusted to 0.1 μM or 1 μM (prepared using 50% MeOH) (25 μl) were added to the wells containing the above solid phase antibody and allowed to compete at room temperature for one hour. Then, peroxidase (HRPO)-labeled streptavidin diluted to 1000-fold (prepared using 0.1% gelatin-PBS (−)) (50 μl) was added to the wells and allowed to react at room temperature for one hour. A TMB (3,3′,5,5′-tetramethylbenzidine) substrate (50 μl) was added to the wells to cause color development, the reaction was terminated by adding an equal volume of 1M $H_3PO_4$, and the absorbance was measured with an ELISA reader at 450 nm (measuring wavelength) and at 655 nm (control wavelength).

Reaction values were plotted as a function of the amounts of unlabeled PAH added, and a PAH amount (unlabeled PAH added)-reaction curve was prepared (FIGS. 3 to 6). In these figures, the information on each curve shows concentration of solid phase antibody (μg/ml)/dilution rate of labeled PAH (m=million). Based on these figures, reaction conditions regarded as optimal were selected (Table 3). In this context, respective reactions were carried out by n=3, blank values were determined by n=6, and identification limits were set at ±3SD.

TABLE 3

Optimal conditions for measuring systems using monoclonal antibodies

| Antibody name | Amount of solid phase antibody | Biotin-labeled PAH | Developing time of TMB |
|---|---|---|---|
| MPAH-1 | 10 μg/ml | Bio-Phe 0.8 μM | 13–15 min. |
| MPAH-3 | 10 μg/ml | Bio-Phe 0.27 μM | 5–8 min |
| MPAH-6 | 5 μg/ml | Bio-Bp 0.008 μM | 7–10 min |
| MPAH-7 | 5 μg/ml | Bio-Bp 0.08 μM | 7–10 min |

(2) Investigation of specificity to PAH standards

Under the optimal conditions determined in the above section (1), the purified monoclonal antibodies were investigated for the cross-reactivity with the following PAH standards (EPA standard components) as well as the ability to distinguish PAH groups different in cycle numbers when grouping the PAH standards into tricyclic, tetracyclic, pentacyclic or hexacyclic PAHs.

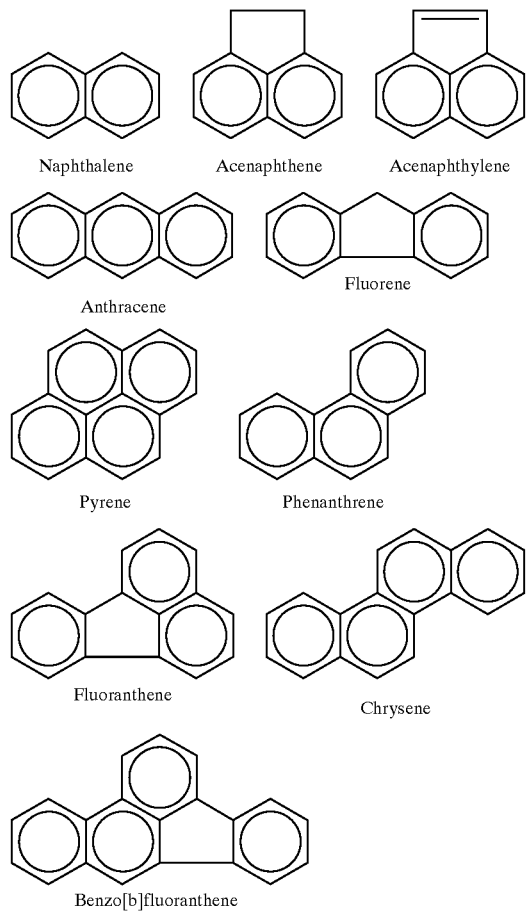

-continued

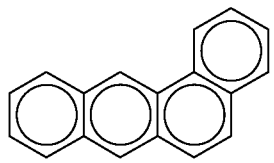
Benzo[a]anthracene

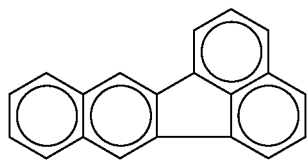
Benzo[k]fluoranthene

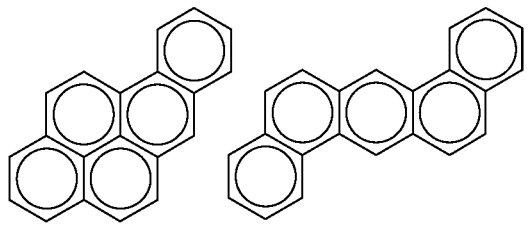
Benzo[a]pyrene    Dibenzo[a, h]anthracene

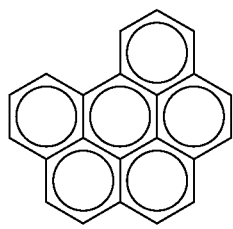
Benzo[g, h, i]perylene

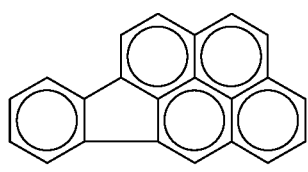
Indeno[1, 2, 3, cd]pyrene (2a) Cross-reactivity with PAH standards

Using four anti-PAH monoclonal antibodies (MPAH-1, MPAH-3, MPAH-6 and MPAH-7) as a solid phase antibody, the cross-reactivity with totally 12 kinds of compounds was investigated.

These compounds are the following 10 kinds of PAHs:
No. 4 : fluorene (tricyclic);
No. 5 : phenanthrene (tricyclic);
No. 6 : anthracene (tricyclic);
No. 7 : fluoranthene (tetracyclic);
No. 8 : pyrene (tetracyclic);
No. 9 : benzo[a]anthracene (tetracyclic);
No. 10: chrysene (tetracyclic);
No. 13: benzo[a]pyrene (pentacyclic);
No. 14: dibenzo[a,h]anthracene (pentacyclic); and
No. 15: benzo[g,h,i]perylene (hexacyclic);
as well as the following 2 kinds of compounds regarded as decomposition products of benzo[a]pyrene:
No. 17: 1-hydroxy-2-naphthoic acid (bicyclic); and
No. 18: 2-hydroxy-3-naphthoic acid (bicyclic).

As a result, it was found that any of four anti-PAH monoclonal antibodies investigated did not recognize the decomposition products of benzo[a]pyrene (compounds of Nos. 17 and 18).

Figure 7:
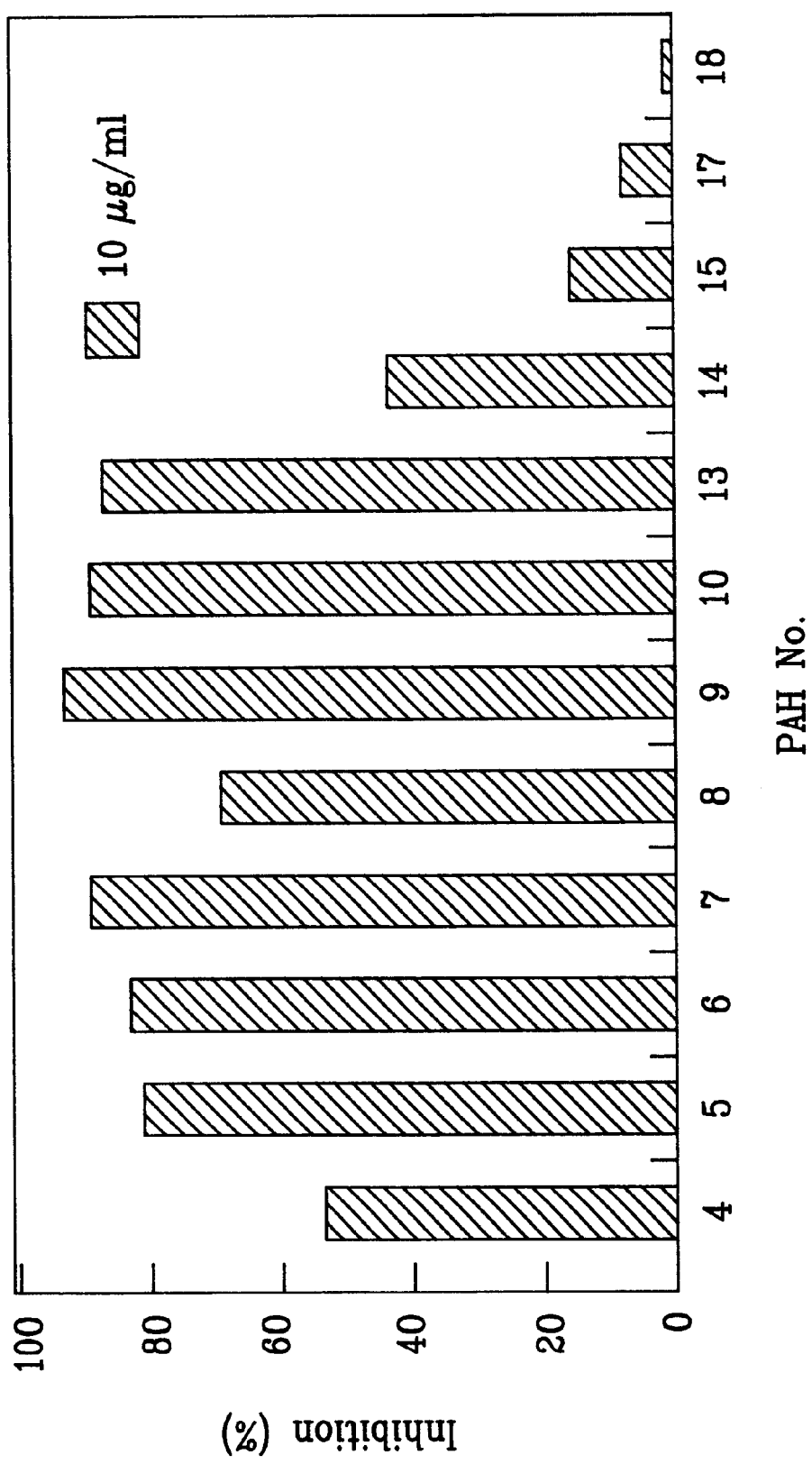
FIG. 7 is a graph showing a cross-reactivity of monoclonal antibody MPAH-1 with PAH standards.

Antibody MPAH-1 recognized all the PAHs excepting the compound of No. 15 (hexacyclic PAH) in a relatively equal manner (FIG. 7).

Figure 8:
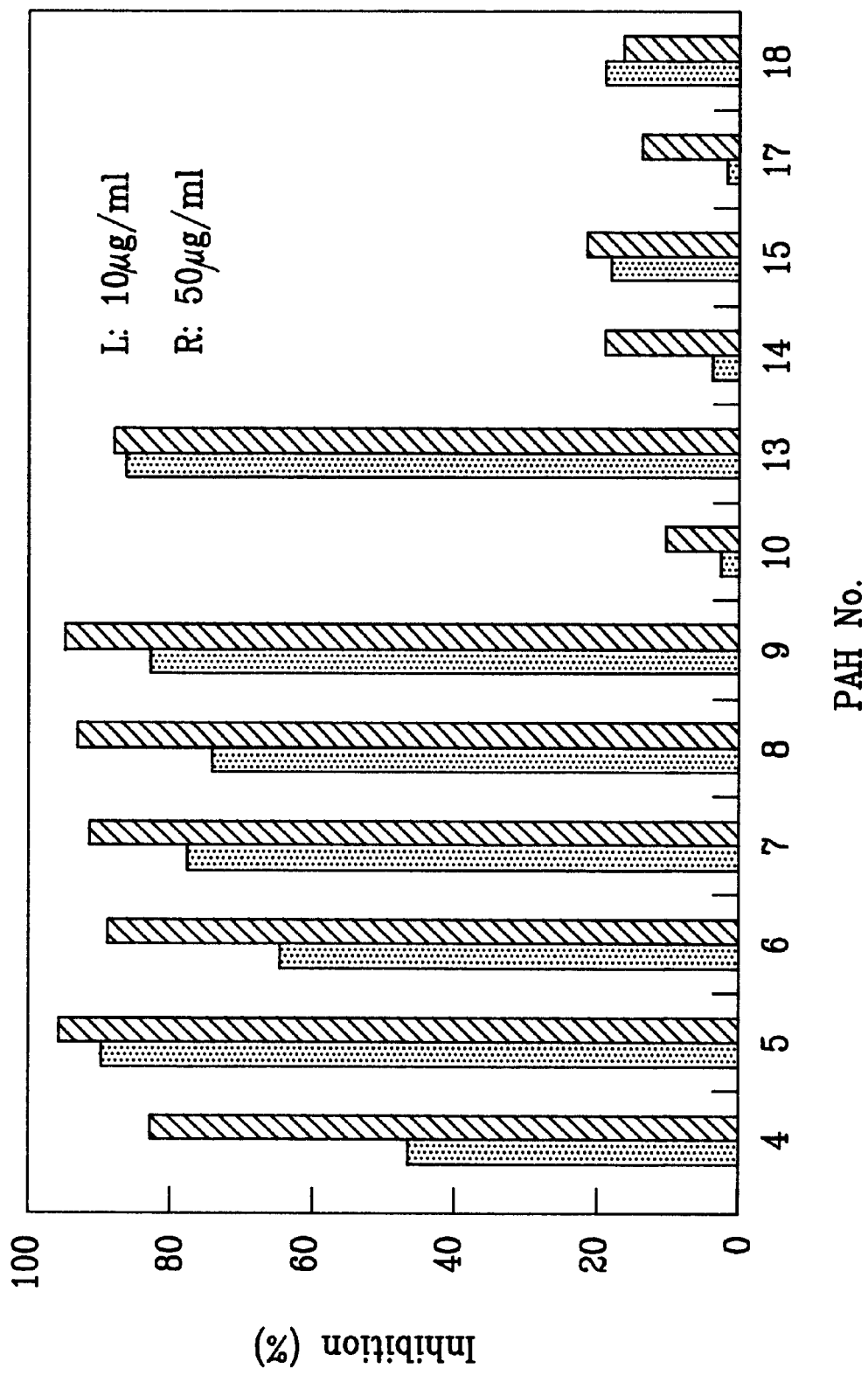
FIG. 8 is a graph showing a cross-reactivity of monoclonal antibody MPAH-3 with PAH standards.

Antibody MPAH-3 equally recognized the tricyclic and tetracyclic PAHs excepting the compound of No. 10 (tetracyclic PAH), and did not recognize the pentacyclic and hexacyclic PAHs excepting the compound of No. 13 (pentacyclic PAH) (FIG. 8). Accordingly, there is a possibility that the tricyclic and tetracyclic PAHs can be specifically analyzed using the antibody.

Figure 9:
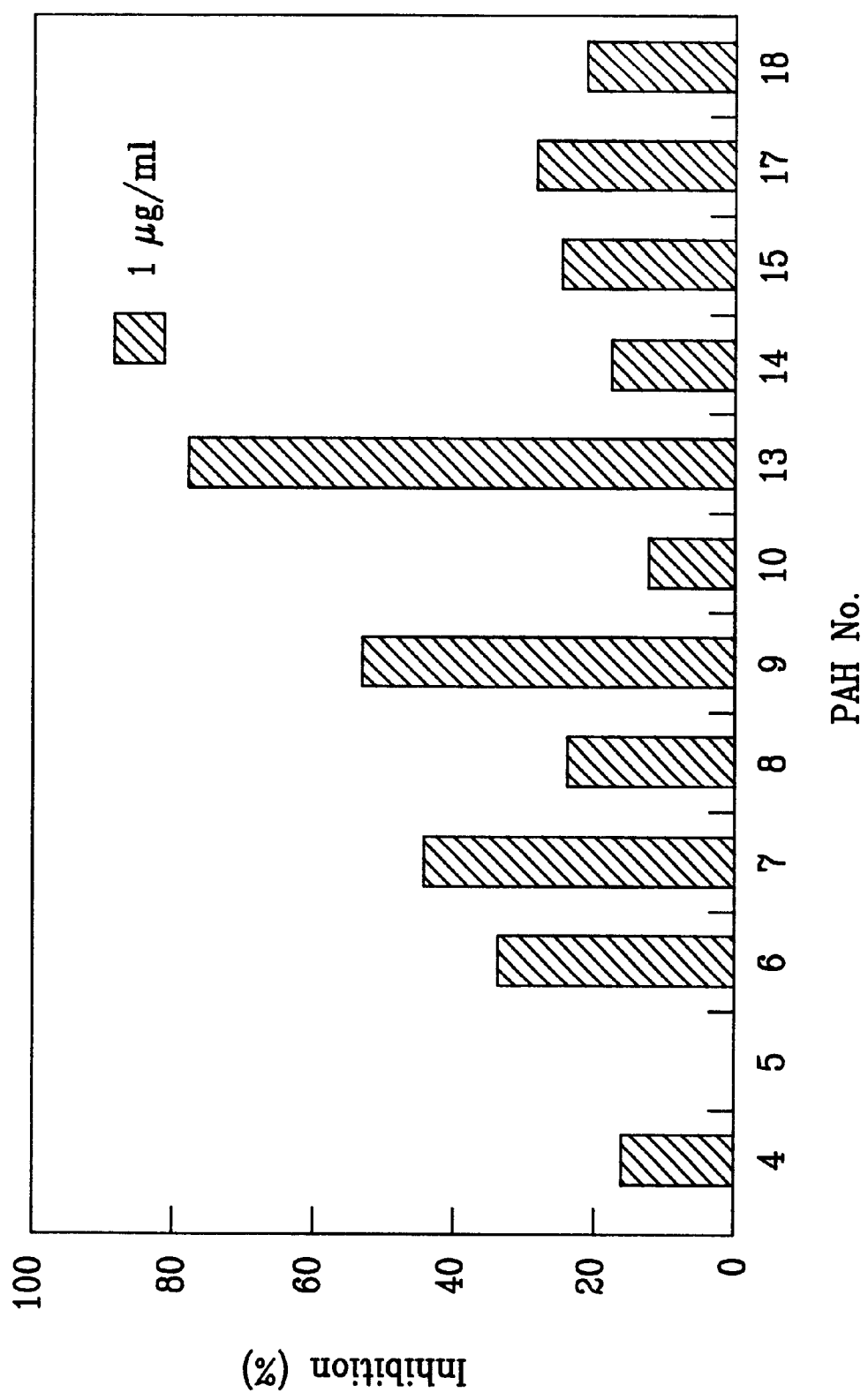
FIG. 9 is a graph showing a cross-reactivity of monoclonal antibody MPAH-6 with PAH standards.

Antibody MPAH-6 showed a high specificity to benzo[a] pyrene (compound of No. 13) among the 12 kinds of compounds investigated (FIG. 9). In addition, antibody MPAH-6 had a low cross-reactivity with the other PAHs, although it cross-reacted with benzo[a]anthracene (compound of No. 9). Thus, this suggested a possibility that benzo[a]pyrene can be specifically analyzed using the antibody.

Figure 10:
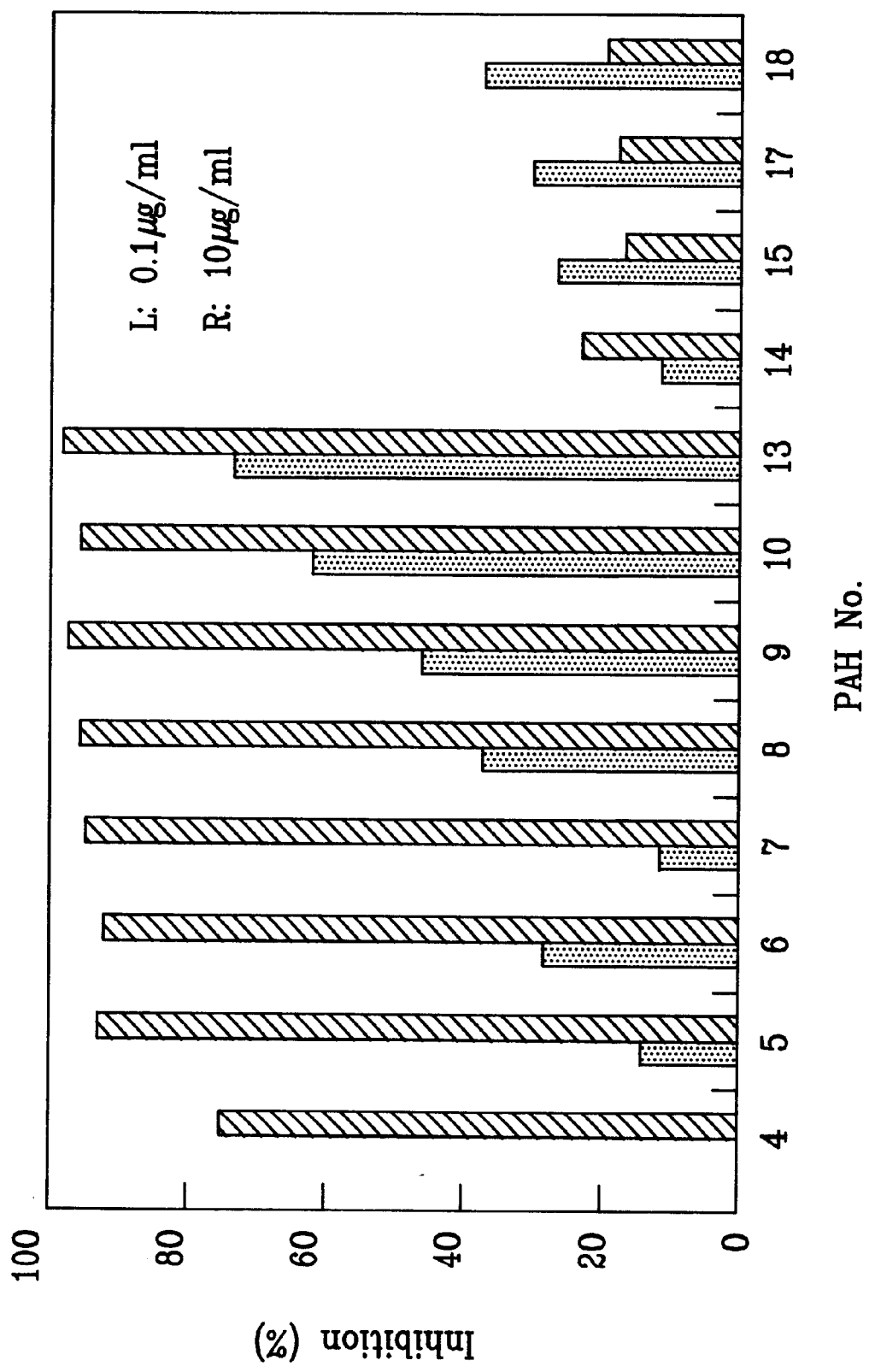
FIG. 10 is a graph showing a cross-reactivity of monoclonal antibody MPAH-7 with PAH standards.

Antibody MPAH-7 showed a specificity to the tetracyclic and pentacyclic PAHs at a low concentration (0.1 µg/ml), but it showed a reactivity to all the PAHs excepting the compound of No. 14 (pentacyclic PAH) and the compound of No. 15 (hexacyclic PAH) at a high concentration (10 µg/ml) (FIG. 10). Thus, this suggested a possibility that all the PAHs can be quantified using the antibody MPAH-1 or MPAH-7.

(2b) Ability to distinguish PAH groups different in cycle numbers

Next, the tricyclic (3R), tetracyclic (4R), pentacyclic (5R) and hexacyclic (6R,) PAHs were mixed as shown below, and the resulting PAH mixtures were dissolved in aqueous 50% MeOH at an initial concentration of 0.05 to 5 µM. MPAH-3 or MPAH-6 was used as a solid phase antibody, the PAH mixtures were analyzed under the optimal conditions of each antibody, and the reactivity of these antibodies was compared.

3R PAH group:
  fluorene, phenanthrene, and anthracene;
4R PAH group:
  fluoranthene, pyrene, and benzo[a]anthracene;
5R+6R PAH group:
  benzo[a]pyrene, dibenzo[a,h]anthracene, and
  benzo[g,h,i]perylene.

Figure 11:
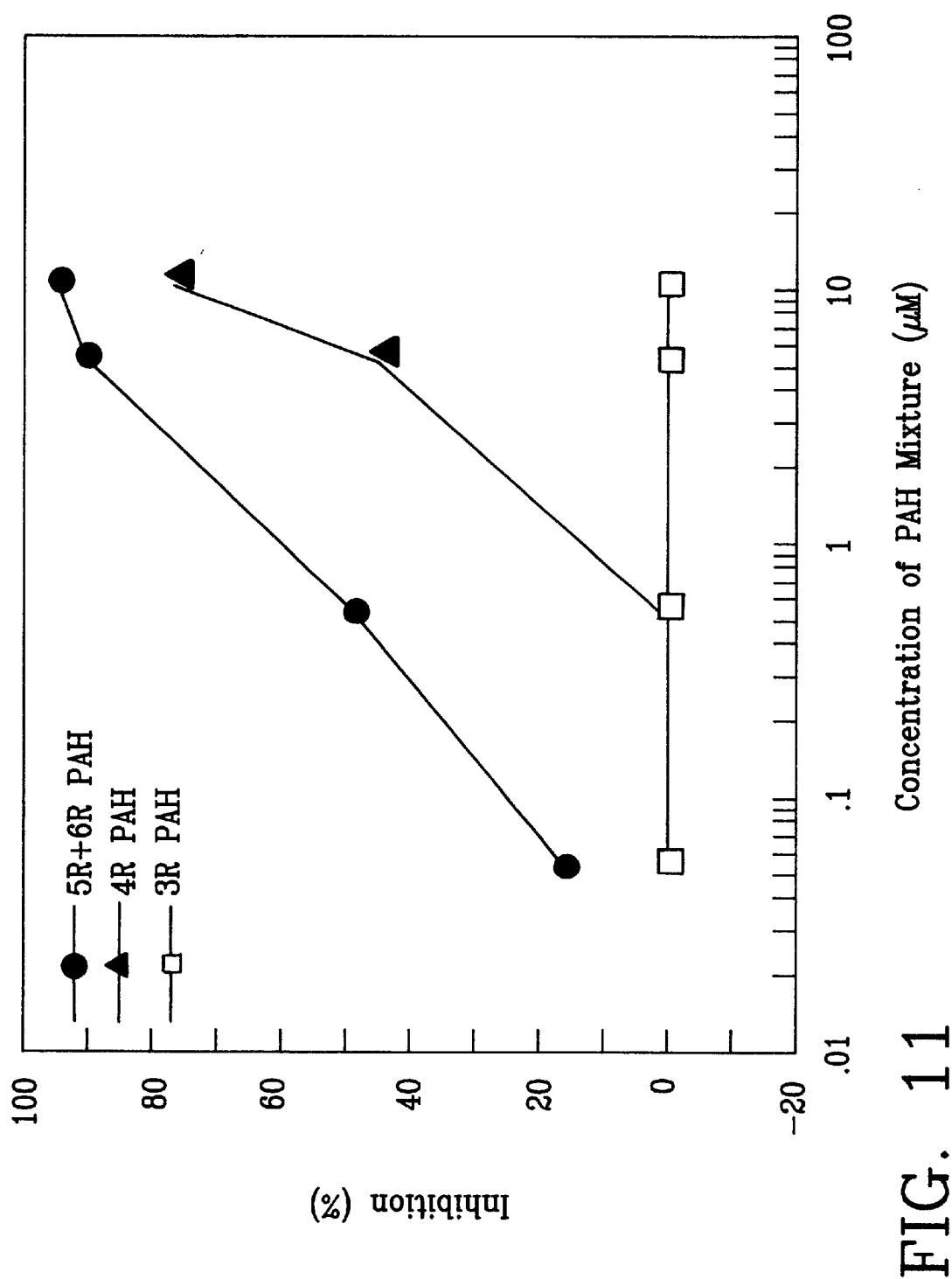
FIG. 11 is a graph showing the results of determining an ability to distinguish PAH groups different in cycle numbers using monoclonal antibody MPAH-6.

As shown in FIG. 11, antibody MPAH-6 showed a reactivity to the 5R+6R PAH group in a concentration-depending manner. In addition, antibody MPAH-6 showed a cross-reactivity to the 4R PAH group at a level of about 1/10 of the reactivity to the 5R+6R PAH group, but it did not show any reactivity to the 3R PAH group at a concentration of less than 10 µM. The results suggest that the 5R+6R PAH group can be quantified using antibody MPAH-6.

Figure 12:
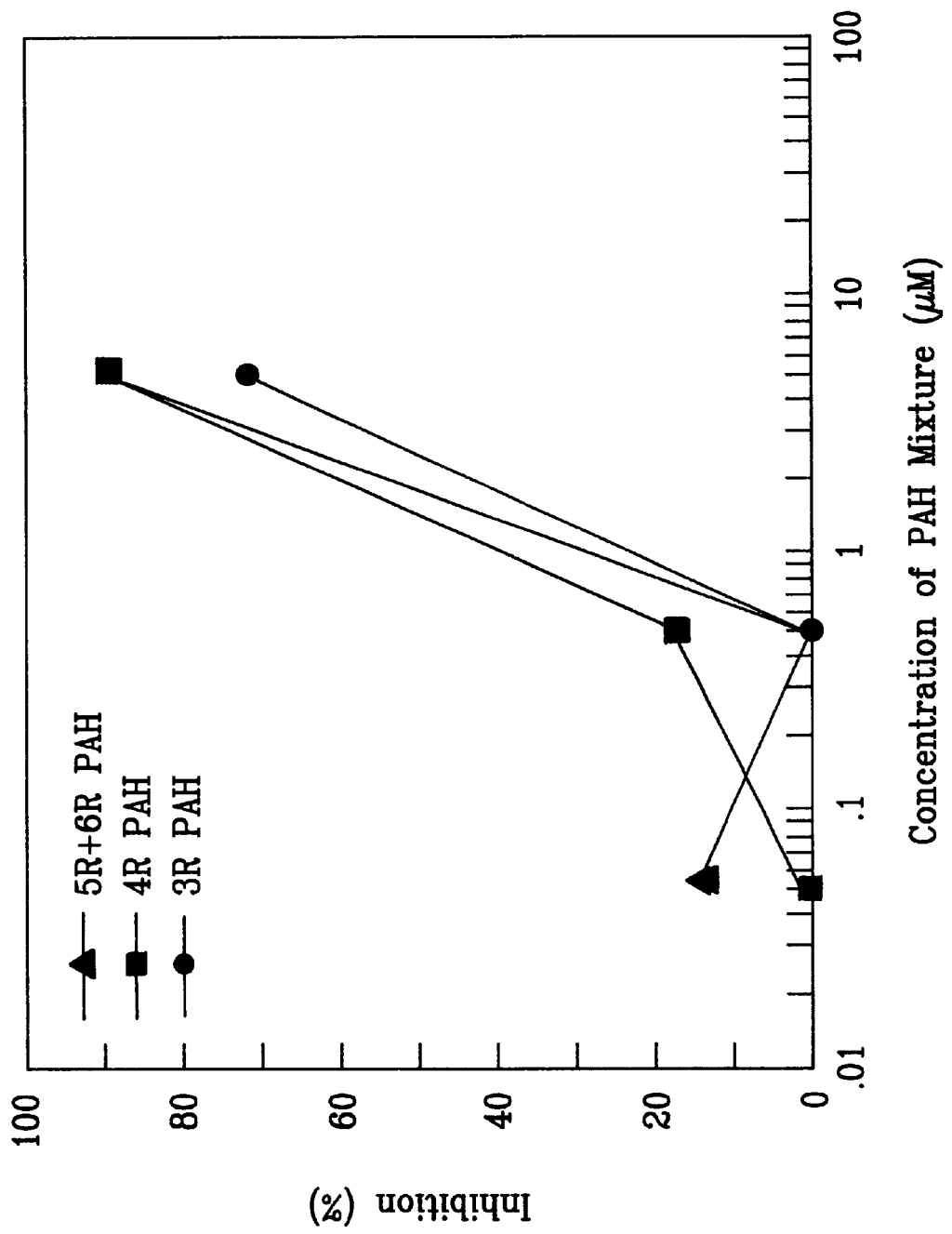
FIG. 12 is a graph showing the results of determining an ability to distinguish PAH groups different in cycle numbers using monoclonal antibody MPAH-3.

On the other hand, antibody MPAH-3 showed an almost equal reactivity to three PAH groups (FIG. 12). The result suggests that all the PAHs can be quantified using antibody MPAH-3.

INDUSTRIAL UTILIZATION

As described above, monoclonal antibodies having a high affinity for PAHs were provided by the present invention. By utilizing the present monoclonal antibodies, it is possible to construct an immunoassay for PAHs which has a high sensitivity and a high accuracy and also allows a rapid measurement. Such an immunoassay can be used, for example, for the following purposes:

(1) Monitoring of all oil components in an industrial waste;
(2) Monitoring of a PAH contamination when carrying out an examination of water quality;
(3) Monitoring of PAHs such as benzo[a]pyrene contained in an exhaust gas from a diesel engine or the like;
(4) Monitoring of PAHs such as benzo[a]pyrene in a room discharged from a heater such as an oil stave;
(5) Monitoring of PAHs such as benzo[a]pyrene contained in a river sludge or a lower sludge of lakes and marshes; and
(6) Monitoring of PAHs such as benzo[a]pyrene contained in an exhaust gas or a drained water (exhaust gas washed water) from a factory incinerating a municipal waste.

What is claimed is:

1. A monoclonal antibody specifically recognizing polycyclic aromatic compounds selected from the group consising of monoclonal antibodies MPAH-1, MPAH-3, MPAH-6 and MPAH-7 which are produced from hybridoma cell lines PAH-1 having accession number FERM BP-6246, PAH-3 having accession number FERM BP-6247, PAH-6 having accession number FERM BP-6248, and PAH-7 having accession number FERM BP-6249, respectively.

2. A hybridoma cell line producing a monoclonal antibody according to claim 1, which is selected from the group consisting of hybridoma cell lines PAH-1 having accession number FERM BP-6246, PAH-3 having accession number FERM BP-6247, PAH-6 having accession number FERM BP-6248, and PAH-7 having accession number FERM BP-6249.

3. An immunoassay for analyzing polycyclic aromatic compounds in a sample, which comprises:

(a) carrying out an antigen-antibody reaction of a sample containing polycyclic aromatic compounds with a monoclonal antibody according to claim 1 in an aqueous solution containing an organic solvent; and
(b) detecting the polycyclic aromatic compounds bound to the antibody.

* * * * *